US006582925B1

United States Patent

(12) United States Patent
Jackson et al.

(10) Patent No.: US 6,582,925 B1
(45) Date of Patent: Jun. 24, 2003

(54) **DESATURASE ANTIGEN OF *MYCOBACTERIUM TUBERCULOSIS***

(75) Inventors: Mary Jackson, Paris (FR); Brigitte Gicquel, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/230,485

(22) PCT Filed: Jul. 25, 1997

(86) PCT No.: PCT/IB97/00923

§ 371 (c)(1),
(2), (4) Date: Apr. 20, 1999

(87) PCT Pub. No.: WO98/04711

PCT Pub. Date: Feb. 5, 1998

Related U.S. Application Data

(60) Provisional application No. 60/022,713, filed on Jul. 26, 1996.

(51) Int. Cl.[7] .................... G01N 33/53; G01N 33/567; A61K 39/04; A61K 39/02; A61K 39/00

(52) U.S. Cl. .................. 435/7.1; 424/139.1; 424/150.1; 424/163.1; 424/168.1; 424/184.1; 424/185.1; 424/190.1; 424/234.1; 424/248.1; 435/7.2; 530/300; 530/350

(58) Field of Search ........................... 424/139.1, 150.1, 424/163.1, 168.1, 184.1, 185.1, 190.1, 234.1, 248.1; 435/7.1, 7.2; 530/300, 350

(56) References Cited

U.S. PATENT DOCUMENTS

| | | | | |
|---|---|---|---|---|
| 6,010,855 A | | 1/2000 | Jackson et al. | 435/6 |
| 6,204,038 B1 | * | 3/2001 | Jackson et al. | |
| 6,248,581 B1 | | 6/2001 | Gicquel et al. | |

FOREIGN PATENT DOCUMENTS

| | | | |
|---|---|---|---|
| WO | WO 92 16652 A | 10/1992 | C12Q/1/68 |
| WO | WO 94 00493 A | 1/1994 | C07K/15/04 |
| WO | WO 95 14713 A | 1/1995 | C07K/14/35 |

OTHER PUBLICATIONS

Sequence search, SEQ ID No.:2, ran Apr. 30, 2002.*

Lim et al., "Identification of *Mycobacterium Tuberculosis* DNA Sequences Encoding Exported Proteins by Using phoA Gene Fusions", J. of Bact., vol. 177, No. 1, pp. 59–65 (1995).

Eiglmeier et al., "Use of an Ordered Cosmid Library to Deduce the Genomic Organization of *Mycobacterium Leprae*", Embl. seq. data library, Jun. 16, 1996, Accession No. L78822.

Jackson et al., Embl. Sequence Data Library, Jul. 31, 1996, Accession No. U49839.

Jackson et al., "*Mycobacterium Tuberculosis* Des Protein: An Immunodominant Target for the Humoral Response of Tuberculous Patients", Infect. & Immunity, vol. 65, No. 7, pp. 2883–2889 (1997).

U.S. Patent Application S.N. 09/429,370 filed Oct. 28, 1999.

Philipp et al., "An integrated map of the genome of the *tubercle bacillus, Mycobacterium tuberculosis* H37Rv, and comparison with *Mycobacterium leprae*", Proc. Nat'l. Acad. Sci, U.S.A. vol. 93, pp. 3132–3137 (Apr. 1996).

* cited by examiner

*Primary Examiner*—Rodney P Swartz
(74) *Attorney, Agent, or Firm*—Finnegan, Henderson, Farabow, Garrett & Dunner, L.L.P.

(57) ABSTRACT

The use of genetic methodology based on the fusion of the proteins with the alcaline phosphatase (Lim et al., 1995) has allowed the isolation of a new exported protein of *M. tuberculosis*. In the present article, first of all the isolation of a gene encoding this exported protein called DES is described as well as its characterization and its distribution among the different mycobacterial species. It is notably shown that the protein has in its primary sequence amino acids only found at the level of active sites of enzymes of class II diiron-oxo proteins family. Among the proteins of this family, DES protein of *M. tuberculosis* does not present significative homologies with stearoyl ACP desaturases. Secondly, the antigenic feature of this protein has been studied. For this, DES protein of *M. tuberculosis* has been overexpressed in *E. coli* under recombinant and purified protein form from this bacterium. The reactivity of tuberculous patients sera infected by *M. tuberculosis* or *M. bovis* against DES protein in Western blot experimentations has been tested. 100% of the tested patients did recognize the protein. The intensity of the antibody response against DES protein measured by ELISA of tuberculous patients sera compared with the one relating to sera patients suffering from other pathologies show that there is a significative difference between the intensity of the antibody responses of these two categories of patients. Accordingly, DES protein is a potentially interesting tool for the tuberculosis serodiagnostic.

4 Claims, 12 Drawing Sheets

```
SEQ ID NO: 1
  1 GATCATCATCGGCCGGCTGCCGCGCAGGGCGCCGACACCGGCGAGTGCGGGCGCGAGGATCGGCCCCCAC

 71 CAGTTCGGCAGCTGCGTGTCGATGCGCTCCACAATCCCGGGAAACAGCTCGACCATTACCTCCTCAATAT

141 GAGCCTCGAAAAACTTGCCGCTGTGCGCGGCGTCGTGGTGAGCGCACACAACAACTGTTAGCTGACCAGC

211 AGGATCGGCGCTCTTACCGGTCTGTTCACCGCATATCTGAACGGACGGCTGGGAGCCACCCGCAAGCAAT

281 TCATCGACTACTGCGTCAACATGTTGCTCAGCACCGCCGCCACCTACGCACCGCACCGCGAGCGGGGAGA

351 ATCCGAACACTCCATCCCAGCCGGGCCGCACAACTGAGGACGACTGGGGTTCACCCCACGCGGCCACCGG


421 CGCCCGCCGATGCCAGCATCCTGCCCGCTGCTGGCAGCTCAACATGCCGCGCGAAGCCCAAACTTGATGC

491 TACCGAGAGACACAGATATATTGACTGCAACCATTAGACACAGATAACTGGAGGCGCCATGTCAGCCAAG
                                                       SEQ ID NO: 2 M  S  A  K

561 CTGACCGACCTGCAGCTGCTGCACGAACTTGAACCGGTCGTCGAGAAGTACCTGAACCGGCACCTGAGCA
    L  T  D  L  Q  L  L  H  E  L  E  P  V  V  E  K  Y  L  N  R  H  L  S  M

631 TGCACAAGCCCTGGAACCCGCACGACTACATCCCGTGGTCGGACGGGAAGAACTACTACGCGCTCGGCGG
      H  K  P  W  N  P  H  D  Y  I  P  W  S  D  G  K  N  Y  Y  A  L  G  G

701 GCAGGATTGGGACCCCGACCAGAGCAAGCTTTCTGATGTCGCCCAGGTGGCGATGGTGCAGAACCTGGTC
     Q  D  W  D  P  D  Q  S  K  L  S  D  V  A  Q  V  A  M  V  Q  N  L  V

771 ACCGAGGACAACCTGCCGTCGTATCACCGCGAGATCGCGATGAACATGGGCATGGACGGCGCGTGGGGGC
    T  E  D  N  L  P  S  Y  H  R  E  I  A  M  N  M  G  M  D  G  A  W  G  Q

841 AGTGGGTCAACCGTTGGACCGCCGAGGAGAATCGGCACGGCATCGCGCTGCGCGACTACCTGGTGGTGAC
      W  V  N  R  W  T  A  E  E  N  R  H  G  I  A  L  R  D  Y  L  V  V  T

911 CCGATCGGTCGACCCTGTCGAGTTGGAGAAACTTCGCCTCGAGGTAGTCAACCGGGGCTTCAGCCCAGGC
     R  S  V  D  P  V  E  L  E  K  L  R  L  E  V  V  N  R  G  F  S  P  G
```

FIG. 2A

```
 981 CAAAACCACCAGGGCCACTATTTCGCGGAGAGCCTCACCGACTCCGTCCTCTATGTCAGTTTCCAGGAAC
     Q  N  H  Q  G  H  Y  F  A  E  S  L  T  D  S  V  L  Y  V  S  F  Q  E  L

1051 TGGCAACCCGGATTTCGCACCGCAATACCGGCAAGGCATGTAACGACCCCGTCGCCGACCAGCTCATGGC
       A  T  R  I  S  H  R  N  T  G  K  A  C  N  D  P  V  A  D  Q  L  M  A

1121 CAAGATCTCGGCAGACGAGAATCTGCACATGATCTTCTACCGCGACGTCAGCGAGGCCGCGTTCGACCTC
      K  I  S  A  D  E  N  L  H  M  I  F  Y  R  D  V  S  E  A  A  F  D  L

1191 GTGCCCAACCAGGCCATGAAGTCGCTGCACCTGATTTTGAGCCACTTCCAGATGCCCGGCTTCCAAGTAC
     V  P  N  Q  A  M  K  S  L  H  L  I  L  S  H  F  Q  M  P  G  F  Q  V  P

1261 CCGAGTTCCGGCGCAAAGCCGTGGTCATCGCCGTCGGGGGTGTCTACGACCCGCGCATCCACCTCGACGA
       E  F  R  R  K  A  V  V  I  A  V  G  G  V  Y  D  P  R  I  H  L  D  E

1331 AGTCGTCATGCCGGTACTGAAGAAATGGTGTATCTTCGAGCGCGAGGACTTCACCGGCGAGGGGGCTAAG
      V  V  M  P  V  L  K  K  W  C  I  F  E  R  E  D  F  T  G  E  G  A  K

1401 CTGCGCGACGAGCTGGCCCTGGTGATCAAGGACCTCGAGCTGGCCTGCGACAAGTTCGAGGTGTCCAAGC
     L  R  D  E  L  A  L  V  I  K  D  L  E  L  A  C  D  K  F  E  V  S  K  Q

1471 AACGCCAACTCGACCGGGAAGCCCGTACGGGCAAGAAGGTCAGCGCACACGAGCTGCATAAAACCGCTGG
       R  Q  L  D  R  E  A  R  T  G  K  K  V  S  A  H  E  L  H  K  T  A  G

1541 CAAACTGGCGATGAGCCGTCGTTAGCCCGGCGACGATGCAGAGCGCGCAGCGCGATGAGCAGGAGGCGGG
       K  L  A  M  S  R  R  *

1611 CAATCCAACCCAGCCCGGCGACGATGCAGAGCGCGCAGCGCGATGAGCAGGAGGTGGGCAATCCAACCCA

1681 GCCCGGCGTTG
```

FIG. 2B

Fe A site
B Helix C Helix

Ribonucleotide reductases

| | | | | | | | | | | | | |
|---|---|---|---|---|---|---|---|---|---|---|---|---|
| v01555 | 049 | EFYKFLFTFL | AMA | E | KLVNFN | IDELVTSFES | HDIDHYYTEQKAM | | ENVH | GETYA | 099 | SEQ ID NO: 5 |
| k02672 | 072 | IFISNLKYQT | LL | D | SIQGRSP | NVALLPLISI | PELETWVETWAFS | | ETIH | SRSYT | 123 | SEQ ID NO: 6 |

Hydrocarbon hydroxylases

| | | | | | | | | | | | | |
|---|---|---|---|---|---|---|---|---|---|---|---|---|
| m58499 | 102 | ETMKVVSNFL | EVG | E | YNAIAA | TGMLWDSAQA | AEQKNGYLAQVL | D | EIRH | THQCA | 152 | SEQ ID NO: 7 |
| x55394 | 102 | ETMKVISNFL | EVG | E | YNAIAA | SAMLWDSATA | AEQKNGYLAQVL | D | EIRH | THQCA | 152 | SEQ ID NO: 8 |
| m60276 | 097 | NALKLFLTAV | SPL | E | YQAFQG | FSRVGRQFSG | AGARVACQMQAI | D | ELRH | VQTQV | 147 | SEQ ID NO: 9 |
| m65106 | 092 | STLKSHYGAI | AVG | E | YAAVTG | EGRMARFSKA | PGNRNMATFGMM | D | ELRH | GQLQL | 142 | SEQ ID NO: 10 |

Stearoyl-ACP-desaturases

| | | | | | | | | | | | |
|---|---|---|---|---|---|---|---|---|---|---|---|
| m59857 | 133 | LVGDMITEEA | LPTYQTMLNT | LDGVRDETGA | SPTSWAIWTRAWTA | E | ENRH | GDLLN | 184 | SEQ ID NO: 11 |
| m59858 | 133 | LVGDMITEEA | LPTYQTMLNT | LDGVRDETGA | SPTPWAIWTRAWTA | E | ENRH | GDLLN | 184 | SEQ ID NO: 12 |
| m61109 | 133 | LVGDMITEEA | LPTYQTMLNT | LDGVRDETGA | SLTPWAVWTRAWTA | E | ENRH | GDLLH | 184 | SEQ ID NO: 13 |
| x62898 | 136 | LVGDMITEEA | LPTYQTMLNT | LDGAKDETGA | SPTSWAVWTRAWTA | E | ENRH | GDLLN | 187 | SEQ ID NO: 14 |
| x60978 | 135 | LVGDMITEEA | LPTYQTMLNT | LDGVRDETGA | SPTSWAIWTRAWTA | E | ENRH | GDLLN | 186 | SEQ ID NO: 15 |
| m91238 | 130 | LIGDMITEEA | LPTYQTMINT | LDGVRDETGA | TVTPWAIWTRAWTA | E | ENRH | GDLLN | 181 | SEQ ID NO: 16 |
| x70962 | 133 | LVGDMITEEA | LPTYQTMINT | LDGVRDETGA | SLTPWAIWTRAWTA | E | ENRH | GDLLN | 184 | SEQ ID NO: 17 |
| m93115 | 121 | LVGDMITEEA | LPTYMSMLNR | CDGIKDDTGA | QPTSWATWTRAWTA | E | ENRH | GDLLN | 172 | SEQ ID NO: 18 |

*M. tuberculosis* DES protein

| | | | | | | | | | |
|---|---|---|---|---|---|---|---|---|---|
| Mtb.des | 062 | SDVAQVAMVQ | NLVTEDNLPS | YHREIAMNMG | MDGAWGQWVNRWTA | E | ENRH | GIALR | 115 |

FIG. 3A

Fe B site
E Helix F Helix

Ribonuclewtide reductases

```
v01555  145 EKILVFLLI E GIFFISSFYS IALLRVRGLM PGICLANNYISR D ELLH TRAAS 196  SEQ ID NO: 5
k02672  195 LCLMSVNAL E AIRFYVSFAC SFAFAERELM EGNAKIIRLIAR D EALH LTGTQ 246  SEQ ID NO: 6
```

Hydrocarbon hydroxylases

```
m58499  200 CSLNLQLVG E ACFTNPLIVA VTEWAAANGD EITPTVFLSIET D ELRH MANGY 251  SEQ ID NO: 7
x55394  200 CSVNLQLVG D TCFTNPLIVA VTEWAIGNGD EITPTVFLSVET D ELRH MANGY 251  SEQ ID NO: 8
m60276  191 FLTAVSFSF E YVLTNLLFVP FMSGAAYNGD MATVTFGFSAQS D EARH MTLGL 242  SEQ ID NO: 9
m65106  188 VAIMLTFSF E TGFTNMQFLG LAADAAEAGD YTFANLISSIQT D ESRH AQQGG 239  SEQ ID NO: 10
```

Stearoyl-ACP-desaturases

```
m59857  219 YLGFIYTSFQ E RATFISHGN TARQAKEHGD IKLAQICGTIAA D EKRH ETAYT 270  SEQ ID NO: 11
m59858  219 YLGFIYTSFQ E RATFISHGN TARLAKEHGD IKLAQICGTITA D EKRH ETAYT 270  SEQ ID NO: 12
m61109  219 YLGFIYTSFQ E RATFVSHGN TARHAKDHGD VKLAQICGTIAS D EKRH ETAYT 270  SEQ ID NO: 13
x62898  222 YLGFVYTSFQ E RATFVSHGN SARLAKEHGD LKMAQICGIIAS D EKRH ETAYT 273  SEQ ID NO: 14
x60978  221 YLGFIYTSFQ E RATFISHGN TARQAKEHGD LKLAQICGTIAA D EKRH ETAYT 272  SEQ ID NO: 15
m91238  216 YLGFVYTSLR K GVTFVSHGN TARLAKEHGD MKLAQICGSIAA D EKRH ETAYT 267  SEQ ID NO: 16
x70962  219 YLGFIYTSFQ E RATFISHGN TARLAKDHGD MKLAQICGIIAA D EKRH ETAYT 219  SEQ ID NO: 17
m93115  207 YMGFIYTSFQ E RATFISHAN TAKLAQHYGD KNLAQVCGNIAS D EKRH ATAYT 258  SEQ ID NO: 18
```

*M. tuberculosis* DES protein

```
Mtb.des 157 TDSVLYVSFQ E LATRISHRN TGKACNDPVA DQLMAK...ISA D ENLH MIFYR 205
```

FIG. 3B

S: soluble fraction
IS: insoluble fraction

1 GATCATCATCGGCCGGCTGCCGCGCAGGGCGCCGACACCGGCGAGTGCGGGCGCGAGGATCGGCCCCCAC

71 CAGTTCGGCAGCTGCGTGTCGATGCGCTCCACAATCCCGGGAAACAGCTCGACCATTACCTCCTCAATAT

141 GAGCCTCGAAAAACTTGCCGCTGTGCGCGGCGTCGTGGTGAGCGCACACAACAACTGTTAGCTGACCAGC

211 AGGATCGGCGCTCTTACCGGTCTGTTCACCGCATATCTGAACGGACGGCTGGGAGCCACCCGCAAGCAAT

281 TCATCGACTACTGCGTCAACATGTTGCTCAGCACCGCCGCCACCTACGCACCGCACCGCGAGCGGGGAGA

351 ATCCGAACACTCCATCCCAGCCGGGCCGCACAACTGAGGACGACTGGGGTTCACCCCACGCGGCCACCGG

-35

421 GGCCCGCCGATGCCAGCATCCTGCCCGCTGCTGGCAGCTCAACATGCCGCGCGAAGCCCAAAC*TTGATG*C

-10 +1

491 TACCGAGAGACACAGA*TATATT*GACTGCAACCATTAGACACAGATAACT*GGAG*GCGCCATGTCAGCCAAG

M S A K

561 CTGACCGACCTGCAGCTGCTGCACGAACTTGAACCGGTCGTCGAGAAGTACCTGAACCGGCACCTGAGCA

L T D L Q L L H E L E P V V E K Y L N R H L S M

631 TGCACAAGCCCTGGAACCCGCACGACTACATCCCGTGGTCGGACGGGAAGAACTACTACGCGCTCGGCGG

H K P W N P H D Y I P W S D G K N Y Y A L G G

701 GCAGGATTGGGACCCCGACCAGAGCAAGCTTTCTGATGTCGCCCAGGTGGCGATGGTGCAGAACCTGGTC

Q- D W D P D Q S K L S D V A Q V A M V Q N L V

771 ACCGAGGACAACCTGCCGTCGTATCACCGCGAGATCGCGATGAACATGGGCATGGACGGCGCGTGGGGC

```
841   AGTGGGTCAACCGTTGGACCGCCGAGGAGAATCGGCACGGCATCGCGCTGCGCGACTACCTGGTGGTGAC
        W  V  N  R  W  T  A  E  E  N  R  H  G  I  A  L  R  D  Y  L  V  V  T

911   CCGATCGGTCGACCCTGTCGAGTTGGAGAAACTTCGCCTCGAGGTAGTCAACCGGGGCTTCAGCCCAGGC
       R  S  V  D  P  V  E  L  E  K  L  R  L  E  V  V  N  R  G  F  S  P  G

981   CAAAACCACCAGGGCCACTATTTCGCGGAGAGCCTCACCGACTCCGTCCTCTATGTCAGTTTCCAGGAAC
      Q  N  H  Q  G  H  Y  F  A  E  S  L  T  D  S  V  L  Y  V  S  F  Q  E  L

1051  TGGCAACCCGGATTTCGCACCGCAATACCGGCAAGGCATGTAACGACCCCGTCGCCGACCAGCTCATGGC
        A  T  R  I  S  H  R  N  T  G  K  A  C  N  D  P  V  A  D  Q  L  M  A

1121  CAAGATCTCGGCAGACGAGAATCTGCACATGATCTTCTACCGCGACGTCAGCGAGGCCGCGTTCGACCTC
       K  I  S  A  D  E  N  L  H  M  I  F  Y  R  D  V  S  E  A  A  F  D  L

1191  GTGCCCAACCAGGCCATGAAGTCGCTGCACCTGATTTTGAGCCACTTCCAGATGCCCGGCTTCCAAGTAC
      V  P  N  Q  A  M  K  S  L  H  L  I  L  S  H  F  Q  M  P  G  F  Q  V  P

1261  CCGAGTTCCGGCGCAAAGCCGTGGTCATCGCCGTCGGGGGTGTCTACGACCCGCGCATCCACCTCGACGA
        E  F  R  R  K  A  V  V  I  A  V  G  G  V  Y  D  P  R  I  H  L  D  E

1331  AGTCGTCATGCCGGTACTGAAGAAATGGTGTATCTTCGAGCGCGAGGACTTCACCGGCGAGGGGGCTAAG
       V  V  M  P  V  L  K  K  W  C  I  F  E  R  E  D  F  T  G  E  G  A  K

1401  CTGCGCGACGAGCTGGCCCTGGTGATCAAGGACCTCGAGCTGGCCTGCGACAAGTTCGAGGTGTCCAAGC
      L  R  D  E  L  A  L  V  I  K  D  L  E  L  A  C  D  K  F  E  V  S  K  Q

1471  AACGCCAACTCGACCGGGAAGCCCGTACGGGCAAGAAGGTCAGCGCACACGAGCTGCATAAAACCGCTGG
        R  Q  L  D  R  E  A  R  T  G  K  K  V  S  A  H  E  L  H  K  T  A  G

1541  CAAACTGGCGATGAGCCGTCGTTAGCCCGGCGACGATGCAGAGCGCGCAGCGCGATGAGC
       K  L  A  M  S  R  R  *
```

FIG. 7B

| Strain or plasmid | Relevant characteristics |
|---|---|
| *E. coli* DH5α | F/endA1 hsdR17($r_k^-m_k^-$) supE44 thi-1 recA1 gyrA ($NaI^r$) relAI Δ(lacZYA-argF)UI69 deoR (Φ80fdlacΔ(lacZ)M15) |
| *E. coli* BL21(DE3)pLysS | F- ompT $hsdS_B(r_B-m_B-$; an *E. coli* B strain) with a λ prophage carrying the T7 RNA polymerase gene. |
| *M. smegmatis* $mc^2155$ | High transformation mutant of *M. smegmatis* ATCC607 |
| *M. tuberculosis* H37Rv | Virulent strain of mycobacterium originally isolated from tuberculosis patient |
| pBluescript KS- | Phagemid derived from pUC19 cloning vector |
| pYUB18 | $(Km)^R$ shuttle vector used for the construction of a *M. tuberculosis* cosmid library |
| pJEM11 | *E.coli*-mycobacterium shuttle vector carrying a truncated *phoA* gene |
| pET14b | pBR322 derivative containing a T7 promoter for expression of target DNAs. |
| pExp421 | pJEM11 vector carrying the 1.1 kb insert from the *des-PhoA* fusion |
| pBS-des | pBluescript KS- vector carrying the *EcoRV* 4.5kb insert containing the *des* gene |
| pET-des | pET14b vector carrying the (JD8-JD9)des PCR amplification product |

FIG. 8

1. Pool of sera from tuberculous cattle
2. Pool of sera from lepromatous leprosy patients
3. Individual sera from *M. bovis*-infected tuberculous patients
4. Individual sera from *M. tuberculosis*-infected tuberculous patients

SEQUENCE LISTING

```
<160> NUMBER OF SEQ ID NOS:  18

<210> SEQ ID NO 1
<211> LENGTH: 1691
<212> TYPE: DNA
<213> ORGANISM: Mycoplasm Tuberculosis
<220> FEATURE:
<221> NAME/KEY: CDS
<222> LOCATION: (549)..(1562)

<400> SEQUENCE: 1

gatcatcatc ggccggctgc cgcgcagggc gccgacaccg gcgagtgcgg gcgcgaggat     60

cggcccccac cagttcggca gctgcgtgtc gatgcgctcc acaatcccgg gaaacagctc    120

gaccattacc tcctcaatat gagcctcgaa aaacttgccg ctgtgcgcgg cgtcgtggtg    180

agcgcacaca acaactgtta gctgaccagc aggatcggcg ctcttaccgg tctgttcacc    240

gcatatctga acggacggct gggagccacc cgcaagcaat tcatcgacta ctgcgtcaac    300

atgttgctca gcaccgccgc cacctacgca ccgcaccgcg agcggggaga atccgaacac    360

tccatcccag ccgggccgca caactgagga cgactggggt tcaccccacg cggccaccgg    420

ggcccgccga tgccagcatc ctgcccgctg ctggcagctc aacatgccgc gcgaagccca    480

aacttgatgc taccgagaga cacagatata ttgactgcaa ccattagaca cagataactg    540

gaggcgcc atg tca gcc aag ctg acc gac ctg cag ctg ctg cac gaa ctt     590
         Met Ser Ala Lys Leu Thr Asp Leu Gln Leu Leu His Glu Leu
           1               5                  10

gaa ccg gtc gtc gag aag tac ctg aac cgg cac ctg agc atg cac aag      638
Glu Pro Val Val Glu Lys Tyr Leu Asn Arg His Leu Ser Met His Lys
 15                  20                  25                  30

ccc tgg aac ccg cac gac tac atc ccg tgg tcg gac ggg aag aac tac      686
```

-continued

```
Pro Trp Asn Pro His Asp Tyr Ile Pro Trp Ser Asp Gly Lys Asn Tyr
                35                  40                  45

tac gcg ctc ggc ggg cag gat tgg gac ccc gac cag agc aag ctt tct      734
Tyr Ala Leu Gly Gly Gln Asp Trp Asp Pro Asp Gln Ser Lys Leu Ser
            50                  55                  60

gat gtc gcc cag gtg gcg atg gtg cag aac ctg gtc acc gag gac aac      782
Asp Val Ala Gln Val Ala Met Val Gln Asn Leu Val Thr Glu Asp Asn
        65                  70                  75

ctg ccg tcg tat cac cgc gag atc gcg atg aac atg ggc atg gac ggc      830
Leu Pro Ser Tyr His Arg Glu Ile Ala Met Asn Met Gly Met Asp Gly
    80                  85                  90

gcg tgg ggg cag tgg gtc aac cgt tgg acc gcc gag gag aat cgg cac      878
Ala Trp Gly Gln Trp Val Asn Arg Trp Thr Ala Glu Glu Asn Arg His
 95                 100                 105                 110

ggc atc gcg ctg cgc gac tac ctg gtg gtg acc cga tcg gtc gac cct      926
Gly Ile Ala Leu Arg Asp Tyr Leu Val Val Thr Arg Ser Val Asp Pro
                115                 120                 125

gtc gag ttg gag aaa ctt cgc ctc gag gta gtc aac cgg ggc ttc agc      974
Val Glu Leu Glu Lys Leu Arg Leu Glu Val Val Asn Arg Gly Phe Ser
            130                 135                 140

cca ggc caa aac cac cag ggc cac tat ttc gcg gag agc ctc acc gac     1022
Pro Gly Gln Asn His Gln Gly His Tyr Phe Ala Glu Ser Leu Thr Asp
        145                 150                 155

tcc gtc ctc tat gtc agt ttc cag gaa ctg gca acc cgg att tcg cac     1070
Ser Val Leu Tyr Val Ser Phe Gln Glu Leu Ala Thr Arg Ile Ser His
    160                 165                 170

cgc aat acc ggc aag gca tgt aac gac ccc gtc gcc gac cag ctc atg     1118
Arg Asn Thr Gly Lys Ala Cys Asn Asp Pro Val Ala Asp Gln Leu Met
175                 180                 185                 190

gcc aag atc tcg gca gac gag aat ctg cac atg atc ttc tac cgc gac     1166
Ala Lys Ile Ser Ala Asp Glu Asn Leu His Met Ile Phe Tyr Arg Asp
                195                 200                 205

gtc agc gag gcc gcg ttc gac ctc gtg ccc aac cag gcc atg aag tcg     1214
Val Ser Glu Ala Ala Phe Asp Leu Val Pro Asn Gln Ala Met Lys Ser
            210                 215                 220

ctg cac ctg att ttg agc cac ttc cag atg ccc ggc ttc caa gta ccc     1262
Leu His Leu Ile Leu Ser His Phe Gln Met Pro Gly Phe Gln Val Pro
        225                 230                 235

gag ttc cgg cgc aaa gcc gtg gtc atc gcc gtc ggg ggt gtc tac gac     1310
Glu Phe Arg Arg Lys Ala Val Val Ile Ala Val Gly Gly Val Tyr Asp
    240                 245                 250

ccg cgc atc cac ctc gac gaa gtc gtc atg ccg gta ctg aag aaa tgg     1358
Pro Arg Ile His Leu Asp Glu Val Val Met Pro Val Leu Lys Lys Trp
255                 260                 265                 270

tgt atc ttc gag cgc gag gac ttc acc ggc gag ggg gct aag ctg cgc     1406
Cys Ile Phe Glu Arg Glu Asp Phe Thr Gly Glu Gly Ala Lys Leu Arg
                275                 280                 285

gac gag ctg gcc ctg gtg atc aag gac ctc gag ctg gcc tgc gac aag     1454
Asp Glu Leu Ala Leu Val Ile Lys Asp Leu Glu Leu Ala Cys Asp Lys
            290                 295                 300

ttc gag gtg tcc aag caa cgc caa ctc gac cgg gaa gcc cgt acg ggc     1502
Phe Glu Val Ser Lys Gln Arg Gln Leu Asp Arg Glu Ala Arg Thr Gly
        305                 310                 315

aag aag gtc agc gca cac gag ctg cat aaa acc gct ggc aaa ctg gcg     1550
Lys Lys Val Ser Ala His Glu Leu His Lys Thr Ala Gly Lys Leu Ala
    320                 325                 330

atg agc cgt cgt tagcccggcg acgatgcaga gcgcgcagcg cgatgagcag         1602
Met Ser Arg Arg
335
```

-continued

```
gaggcgggca atccaaccca gcccggcgac gatgcagagc gcgcagcgcg atgagcagga   1662

ggtgggcaat ccaacccagc ccggcgttg                                      1691


<210> SEQ ID NO 2
<211> LENGTH: 338
<212> TYPE: PRT
<213> ORGANISM: Mycoplasm Tuberculosis

<400> SEQUENCE: 2

Met Ser Ala Lys Leu Thr Asp Leu Gln Leu Leu His Glu Leu Glu Pro
  1               5                  10                  15

Val Val Glu Lys Tyr Leu Asn Arg His Leu Ser Met His Lys Pro Trp
             20                  25                  30

Asn Pro His Asp Tyr Ile Pro Trp Ser Asp Gly Lys Asn Tyr Tyr Ala
         35                  40                  45

Leu Gly Gly Gln Asp Trp Asp Pro Asp Gln Ser Lys Leu Ser Asp Val
     50                  55                  60

Ala Gln Val Ala Met Val Gln Asn Leu Val Thr Glu Asp Asn Leu Pro
 65                  70                  75                  80

Ser Tyr His Arg Glu Ile Ala Met Asn Met Gly Met Asp Gly Ala Trp
                 85                  90                  95

Gly Gln Trp Val Asn Arg Trp Thr Ala Glu Glu Asn Arg His Gly Ile
            100                 105                 110

Ala Leu Arg Asp Tyr Leu Val Val Thr Arg Ser Val Asp Pro Val Glu
        115                 120                 125

Leu Glu Lys Leu Arg Leu Glu Val Val Asn Arg Gly Phe Ser Pro Gly
    130                 135                 140

Gln Asn His Gln Gly His Tyr Phe Ala Glu Ser Leu Thr Asp Ser Val
145                 150                 155                 160

Leu Tyr Val Ser Phe Gln Glu Leu Ala Thr Arg Ile Ser His Arg Asn
                165                 170                 175

Thr Gly Lys Ala Cys Asn Asp Pro Val Ala Asp Gln Leu Met Ala Lys
            180                 185                 190

Ile Ser Ala Asp Glu Asn Leu His Met Ile Phe Tyr Arg Asp Val Ser
        195                 200                 205

Glu Ala Ala Phe Asp Leu Val Pro Asn Gln Ala Met Lys Ser Leu His
    210                 215                 220

Leu Ile Leu Ser His Phe Gln Met Pro Gly Phe Gln Val Pro Glu Phe
225                 230                 235                 240

Arg Arg Lys Ala Val Val Ile Ala Val Gly Gly Val Tyr Asp Pro Arg
                245                 250                 255

Ile His Leu Asp Glu Val Val Met Pro Val Leu Lys Lys Trp Cys Ile
            260                 265                 270

Phe Glu Arg Glu Asp Phe Thr Gly Glu Gly Ala Lys Leu Arg Asp Glu
        275                 280                 285

Leu Ala Leu Val Ile Lys Asp Leu Glu Leu Ala Cys Asp Lys Phe Glu
    290                 295                 300

Val Ser Lys Gln Arg Gln Leu Asp Arg Glu Ala Arg Thr Gly Lys Lys
305                 310                 315                 320

Val Ser Ala His Glu Leu His Lys Thr Ala Gly Lys Leu Ala Met Ser
                325                 330                 335

Arg Arg


<210> SEQ ID NO 3
```

-continued

<211> LENGTH: 33
<212> TYPE: DNA
<213> ORGANISM: Artificial Sequence
<220> FEATURE:
<223> OTHER INFORMATION: Description of Artificial Sequence: Oligonucleotide

<400> SEQUENCE: 3
cggcatatgt cagccaagct gaccgacctg cag 33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Oligonucleotide

<400> SEQUENCE: 4
ccgggatccc gcgctcgccg ctctgcatcg tcg 33

<210> SEQ ID NO 5
<211> LENGTH: 104
<212> TYPE: PRT
<213> ORGANISM: Epstein-barr virus

<400> SEQUENCE: 5

```
Glu Phe Tyr Lys Phe Leu Phe Thr Phe Leu Ala Met Ala Glu Lys Leu
  1               5                  10                  15

Val Asn Phe Asn Ile Asp Glu Leu Val Thr Ser Phe Glu Ser His Asp
             20                  25                  30

Ile Asp His Tyr Tyr Thr Glu Gln Lys Ala Met Glu Asn Val His Gly
         35                  40                  45

Glu Thr Tyr Ala Glu Lys Ile Leu Val Phe Leu Leu Ile Glu Gly Ile
     50                  55                  60

Phe Phe Ile Ser Ser Phe Tyr Ser Ile Ala Leu Leu Arg Val Arg Gly
 65                  70                  75                  80

Leu Met Pro Gly Ile Cys Leu Ala Asn Asn Tyr Ile Ser Arg Asp Glu
                 85                  90                  95

Leu Leu His Thr Arg Ala Ser Ser
            100
```

<210> SEQ ID NO 6
<211> LENGTH: 104
<212> TYPE: PRT
<213> ORGANISM: E. coli

<400> SEQUENCE: 6

```
Ile Phe Ile Ser Asn Leu Lys Tyr Gln Thr Leu Leu Asp Ser Ile Gln
  1               5                  10                  15

Gly Arg Ser Pro Asn Val Ala Leu Leu Pro Leu Ile Ser Ile Pro Glu
             20                  25                  30

Leu Glu Thr Trp Val Glu Thr Trp Ala Phe Ser Glu Thr Ile His Ser
         35                  40                  45

Arg Ser Tyr Thr Leu Cys Leu Met Ser Val Asn Ala Leu Glu Ala Ile
     50                  55                  60

Arg Phe Tyr Val Ser Phe Ala Cys Ser Phe Ala Phe Ala Glu Arg Glu
 65                  70                  75                  80

Leu Met Glu Gly Asn Ala Lys Ile Ile Arg Leu Ile Ala Arg Asp Glu
                 85                  90                  95
```

-continued

```
Ala Leu His Leu Thr Gly Thr Gln
            100


<210> SEQ ID NO 7
<211> LENGTH: 104
<212> TYPE: PRT
<213> ORGANISM: Methylococcus capsulatus

<400> SEQUENCE: 7

Glu Thr Met Lys Val Val Ser Asn Phe Leu Glu Val Gly Glu Tyr Asn
  1               5                  10                  15

Ala Ile Ala Ala Thr Gly Met Leu Trp Asp Ser Ala Gln Ala Ala Glu
             20                  25                  30

Gln Lys Asn Gly Tyr Leu Ala Gln Val Leu Asp Glu Ile Arg His Thr
         35                  40                  45

His Gln Cys Ala Cys Ser Leu Asn Leu Gln Leu Val Gly Glu Ala Cys
     50                  55                  60

Phe Thr Asn Pro Leu Ile Val Ala Val Thr Glu Trp Ala Ala Ala Asn
 65                  70                  75                  80

Gly Asp Glu Ile Thr Pro Thr Val Phe Leu Ser Ile Glu Thr Asp Glu
                 85                  90                  95

Leu Arg His Met Ala Asn Gly Tyr
            100


<210> SEQ ID NO 8
<211> LENGTH: 104
<212> TYPE: PRT
<213> ORGANISM: Methylosinus trichosporium

<400> SEQUENCE: 8

Glu Thr Met Lys Val Ile Ser Asn Phe Leu Glu Val Gly Glu Tyr Asn
  1               5                  10                  15

Ala Ile Ala Ala Ser Ala Met Leu Trp Asp Ser Ala Thr Ala Ala Glu
             20                  25                  30

Gln Lys Asn Gly Tyr Leu Ala Gln Val Leu Asp Glu Ile Arg His Thr
         35                  40                  45

His Gln Cys Ala Cys Ser Val Asn Leu Gln Leu Val Gly Asp Thr Cys
     50                  55                  60

Phe Thr Asn Pro Leu Ile Val Ala Val Thr Glu Trp Ala Ile Gly Asn
 65                  70                  75                  80

Gly Asp Glu Ile Thr Pro Thr Val Phe Leu Ser Val Glu Thr Asp Glu
                 85                  90                  95

Leu Arg His Met Ala Asn Gly Tyr
            100


<210> SEQ ID NO 9
<211> LENGTH: 104
<212> TYPE: PRT
<213> ORGANISM: Pseudomonas sp.

<400> SEQUENCE: 9

Asn Ala Leu Lys Leu Phe Leu Thr Ala Val Ser Pro Leu Glu Tyr Gln
  1               5                  10                  15

Ala Phe Gln Gly Phe Ser Arg Val Gly Arg Gln Phe Ser Gly Ala Gly
             20                  25                  30

Ala Arg Val Ala Cys Gln Met Gln Ala Ile Asp Glu Leu Arg His Val
         35                  40                  45

Gln Thr Gln Val Phe Leu Thr Ala Val Ser Phe Ser Phe Glu Tyr Val
```

-continued

```
     50                  55                  60

Leu Thr Asn Leu Leu Phe Val Pro Phe Met Ser Gly Ala Ala Tyr Asn
 65                  70                  75                  80

Gly Asp Met Ala Thr Val Thr Phe Gly Phe Ser Ala Gln Ser Asp Glu
                 85                  90                  95

Ala Arg His Met Thr Leu Gly Leu
            100


<210> SEQ ID NO 10
<211> LENGTH: 104
<212> TYPE: PRT
<213> ORGANISM: Pseudomonas mendocina

<400> SEQUENCE: 10

Ser Thr Leu Lys Ser His Tyr Gly Ala Ile Ala Val Gly Glu Tyr Ala
  1               5                  10                  15

Ala Val Thr Gly Glu Gly Arg Met Ala Arg Phe Ser Lys Ala Pro Gly
            20                  25                  30

Asn Arg Asn Met Ala Thr Phe Gly Met Met Asp Glu Leu Arg His Gly
        35                  40                  45

Gln Leu Gln Leu Val Ala Ile Met Leu Thr Phe Ser Phe Glu Thr Gly
     50                  55                  60

Phe Thr Asn Met Gln Phe Leu Gly Leu Ala Ala Asp Ala Ala Glu Ala
 65                  70                  75                  80

Gly Asp Tyr Thr Phe Ala Asn Leu Ile Ser Ser Ile Gln Thr Asp Glu
                 85                  90                  95

Ser Arg His Ala Gln Gln Gly Gly
            100


<210> SEQ ID NO 11
<211> LENGTH: 106
<212> TYPE: PRT
<213> ORGANISM: Ricinus communis

<400> SEQUENCE: 11

Leu Val Gly Asp Met Ile Thr Glu Glu Ala Leu Pro Thr Tyr Gln Thr
  1               5                  10                  15

Met Leu Asn Thr Leu Asp Gly Val Arg Asp Glu Thr Gly Ala Ser Pro
            20                  25                  30

Thr Ser Trp Ala Ile Trp Thr Arg Ala Trp Thr Ala Glu Glu Asn Arg
        35                  40                  45

His Gly Asp Leu Leu Asn Tyr Leu Gly Phe Ile Tyr Thr Ser Phe Gln
     50                  55                  60

Glu Arg Ala Thr Phe Ile Ser His Gly Asn Thr Ala Arg Gln Ala Lys
 65                  70                  75                  80

Glu His Gly Asp Ile Lys Leu Ala Gln Ile Cys Gly Thr Ile Ala Ala
                 85                  90                  95

Asp Glu Lys Arg His Glu Thr Ala Tyr Thr
            100                 105


<210> SEQ ID NO 12
<211> LENGTH: 106
<212> TYPE: PRT
<213> ORGANISM: Cucumis sativus

<400> SEQUENCE: 12

Leu Val Gly Asp Met Ile Thr Glu Glu Ala Leu Pro Thr Tyr Gln Thr
  1               5                  10                  15
```

-continued

```
Met Leu Asn Thr Leu Asp Gly Val Arg Asp Glu Thr Gly Ala Ser Pro
            20                  25                  30

Thr Pro Trp Ala Ile Trp Thr Arg Ala Trp Thr Ala Glu Glu Asn Arg
        35                  40                  45

His Gly Asp Leu Leu Asn Tyr Leu Gly Phe Ile Tyr Thr Ser Phe Gln
    50                  55                  60

Glu Arg Ala Thr Phe Ile Ser His Gly Asn Thr Ala Arg Leu Ala Lys
65                  70                  75                  80

Glu His Gly Asp Ile Lys Leu Ala Gln Ile Cys Gly Thr Ile Thr Ala
                85                  90                  95

Asp Glu Lys Arg His Glu Thr Ala Tyr Thr
            100                 105


<210> SEQ ID NO 13
<211> LENGTH: 106
<212> TYPE: PRT
<213> ORGANISM: Carthamus tinctorius

<400> SEQUENCE: 13

Leu Val Gly Asp Met Ile Thr Glu Glu Ala Leu Pro Thr Tyr Gln Thr
  1               5                  10                  15

Met Leu Asn Thr Leu Asp Gly Val Arg Asp Glu Thr Gly Ala Ser Leu
            20                  25                  30

Thr Pro Trp Ala Val Trp Thr Arg Ala Trp Thr Ala Glu Glu Asn Arg
        35                  40                  45

His Gly Asp Leu Leu His Tyr Leu Gly Phe Ile Tyr Thr Ser Phe Gln
    50                  55                  60

Glu Arg Ala Thr Phe Val Ser His Gly Asn Thr Ala Arg His Ala Lys
65                  70                  75                  80

Asp His Gly Asp Val Lys Leu Ala Gln Ile Cys Gly Thr Ile Ala Ser
                85                  90                  95

Asp Glu Lys Arg His Glu Thr Ala Tyr Thr
            100                 105


<210> SEQ ID NO 14
<211> LENGTH: 106
<212> TYPE: PRT
<213> ORGANISM: Spinacia oleracea

<400> SEQUENCE: 14

Leu Val Gly Asp Met Ile Thr Glu Glu Ala Leu Pro Thr Tyr Gln Thr
  1               5                  10                  15

Met Leu Asn Thr Leu Asp Gly Ala Lys Asp Glu Thr Gly Ala Ser Pro
            20                  25                  30

Thr Ser Trp Ala Val Trp Thr Arg Ala Trp Thr Ala Glu Glu Asn Arg
        35                  40                  45

His Gly Asp Leu Leu Asn Tyr Leu Gly Phe Val Tyr Thr Ser Phe Gln
    50                  55                  60

Glu Arg Ala Thr Phe Val Ser His Gly Asn Ser Ala Arg Leu Ala Lys
65                  70                  75                  80

Glu His Gly Asp Leu Lys Met Ala Gln Ile Cys Gly Ile Ile Ala Ser
                85                  90                  95

Asp Glu Lys Arg His Glu Thr Ala Tyr Thr
            100                 105


<210> SEQ ID NO 15
```

-continued

<211> LENGTH: 106
<212> TYPE: PRT
<213> ORGANISM: Brassica sp.

<400> SEQUENCE: 15

```
Leu Val Gly Asp Met Ile Thr Glu Glu Ala Leu Pro Thr Tyr Gln Thr
  1               5                  10                  15

Met Leu Asn Thr Leu Asp Gly Val Arg Asp Glu Thr Gly Ala Ser Pro
             20                  25                  30

Thr Ser Trp Ala Ile Trp Thr Arg Ala Trp Thr Ala Glu Glu Asn Arg
         35                  40                  45

His Gly Asp Leu Leu Asn Tyr Leu Gly Phe Ile Tyr Thr Ser Phe Gln
     50                  55                  60

Glu Arg Ala Thr Phe Ile Ser His Gly Asn Thr Ala Arg Gln Ala Lys
 65                  70                  75                  80

Glu His Gly Asp Leu Lys Leu Ala Gln Ile Cys Gly Thr Ile Ala Ala
                 85                  90                  95

Asp Glu Lys Arg His Glu Thr Ala Tyr Thr
            100                 105
```

<210> SEQ ID NO 16
<211> LENGTH: 106
<212> TYPE: PRT
<213> ORGANISM: Solanum tuberosum

<400> SEQUENCE: 16

```
Leu Ile Gly Asp Met Ile Thr Glu Glu Ala Leu Pro Thr Tyr Gln Thr
  1               5                  10                  15

Met Ile Asn Thr Leu Asp Gly Val Arg Asp Glu Thr Gly Ala Thr Val
             20                  25                  30

Thr Pro Trp Ala Ile Trp Thr Arg Ala Trp Thr Ala Glu Glu Asn Arg
         35                  40                  45

His Gly Asp Leu Leu Asn Tyr Leu Gly Phe Val Tyr Thr Ser Leu Arg
     50                  55                  60

Lys Gly Val Thr Phe Val Ser His Gly Asn Thr Ala Arg Leu Ala Lys
 65                  70                  75                  80

Glu His Gly Asp Met Lys Leu Ala Gln Ile Cys Gly Ser Ile Ala Ala
                 85                  90                  95

Asp Glu Lys Arg His Glu Thr Ala Tyr Thr
            100                 105
```

<210> SEQ ID NO 17
<211> LENGTH: 106
<212> TYPE: PRT
<213> ORGANISM: Linum sp.

<400> SEQUENCE: 17

```
Leu Val Gly Asp Met Ile Thr Glu Glu Ala Leu Pro Thr Tyr Gln Thr
  1               5                  10                  15

Met Leu Asn Thr Leu Asp Gly Val Arg Asp Glu Thr Gly Ala Ser Leu
             20                  25                  30

Thr Pro Trp Ala Ile Trp Thr Arg Ala Trp Thr Ala Glu Glu Asn Arg
         35                  40                  45

His Gly Asp Leu Leu Asn Tyr Leu Gly Phe Ile Tyr Thr Ser Phe Gln
     50                  55                  60

Glu Arg Ala Thr Phe Ile Ser His Gly Asn Thr Ala Arg Leu Ala Lys
 65                  70                  75                  80
```

-continued

```
Asp His Gly Asp Met Lys Leu Ala Gln Ile Cys Gly Ile Ile Ala Ala
                 85                  90                  95

Asp Glu Lys Arg His Glu Thr Ala Tyr Thr
            100                 105


<210> SEQ ID NO 18
<211> LENGTH: 106
<212> TYPE: PRT
<213> ORGANISM: Coriandrum sativum

<400> SEQUENCE: 18

Leu Val Gly Asp Met Ile Thr Glu Glu Ala Leu Pro Thr Tyr Met Ser
  1               5                  10                  15

Met Leu Asn Arg Cys Asp Gly Ile Lys Asp Asp Thr Gly Ala Gln Pro
             20                  25                  30

Thr Ser Trp Ala Thr Trp Thr Arg Ala Trp Thr Ala Glu Glu Asn Arg
         35                  40                  45

His Gly Asp Leu Leu Asn Tyr Met Gly Phe Ile Tyr Thr Ser Phe Gln
     50                  55                  60

Glu Arg Ala Thr Phe Ile Ser His Ala Asn Thr Ala Lys Leu Ala Gln
 65                  70                  75                  80

His Tyr Gly Asp Lys Asn Leu Ala Gln Val Cys Gly Asn Ile Ala Ser
                 85                  90                  95

Asp Glu Lys Arg His Ala Thr Ala Tyr Thr
            100                 105
```

DESATURASE ANTIGEN OF *MYCOBACTERIUM TUBERCULOSIS*

This application is a 371 national stage filing of International Application PCT/IB97/00923, filed Jul. 25, 1997, which claims the benefit of U. S. Provisional Application Ser. No. 60/022,713, filed Jul. 26, 1996.

BACKGROUND OF THE INVENTION

Tuberculosis and leprosy, caused by the bacilli from the *Mycobacterium tuberculosis* complex and *M. leprae* respectively are the two major mycobacterial diseases. Pathogenic mycobacteria have the ability to survive within host phagocytic cells. From the interactions between the host and the bacteria results the pathology of the tuberculosis Infection through the damages the host immune response causes on tissues (Andersen & Brennan, 1994). Alternatively, the protection of the host is also dependent on its interactions with mycobacteria.

Identification of the bacterial antigens involved in these interactions with the immune system is essential for the understanding of the pathogenic mechanisms of mycobacteria and the host immunological response in relation to the evolution of the disease. It is also of great importance for the improvement of the strategies for mycobacterial disease control through vaccination and immunodiagnosis.

Through the years, various strategies have been followed for identifying mycobacterial antigens. Biochemical tools for fractionating and analysing bacterial proteins permitted the isolation of antigenic proteins selected on their capacity to elicit B or T cell responses (Romain et al., 1993; Sorensen et al., 1995). The recent development of molecular genetic methods for mycobacteria (Jacobs et al., 1991; Snapper et al., 1990; Hatful, 1993. Young et al., 1985) allowed the construction of DNA expression libraries of both *M. tuberculosis* and *M. leprae* in the λgt11vector and their expression in *E. coli*. The screening of these recombinant libraries using murine polyclonal or monoclonal antibodies and patient sera led to the identification of numerous antigens (Braibant et al., 1994; Hermans et al., 1995; Thole & van der Zee, 1990). However, most of them turned out to belong to the group of highly conserved heat shock proteins (Thole & van der Zee 1990; Young et al., 1990).

The observation in animal models that specific protection against tuberculosis was conferred only by administration of live BCG vaccine, suggested that mycobacterial secreted proteins might play a major role in inducing protective immunity. These proteins were shown to induce cell mediated immune responses and protective immunity in guinea pig or mice model of tuberculosis (Pal & Horwitz, 1992; Andersen, 1994; Haslow et al., 1995). Recently, a genetic methodology for the identification of exported proteins based on PhoA gene fusions was adapted to mycobacteria by Lim et al. (1995). It permitted the isolation of *M. tuberculosis* DNA fragments encoding exported proteins. Among them, the already known 19 kDa lipoprotein (Lee et al., 1992) and the ERP protein similar to the *M. leprae* 28 kDa antigen (Berthet et al., 1995).

SUMMARY OF THE INVENTION

We have characterized a new *M. tuberculosis* exported protein named DES identified by using the PhoA gene fusion methodology. The des gene, which seems conserved among mycobacterial species, encodes an antigenic protein highly recognized by human sera from both tuberculosis and leprosy patients but not by sera from tuberculous cattle. The amino acid sequence of the DES protein contains two sets of motifs that are characteristical of the active sites of enzymes from the class II diiron-oxo protein family. Among this family, the DES protein presents significant homologies to soluble stearoyl-ACP desaturases.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

The invention will be further clarified by the following examples, which are intended to be purely exemplary of the invention.

Bacteria, Media and Growth Conditions

The bacterial strains and plasmids used in this study are listed in FIG. 8 *E. coli* DH5α of BL21(DE3)pLysS cultures were routinely grown in Luria B medium (Difco) at 37° C. Mycobacterium cultures were grown in Middlebrook 7H9 medium (Difco) supplemented with Tween 0.05%, glycerol (0.2%) and ADC (glucose, 0.2%; BSA fraction V, 0.5%; and NaCl, 0.085%) at 37° C. Antibiotics when required were added at the following concentrations ampicillin (100 μg/ml). kanamycin (20 μg/ml).

Human and Cattle Sera

Serum specimens from 20 individuals with pulmonary or extra-pulmonary tuberculosis (*M. tuberculosis* infected) were obtained from the Bligny sanatorium (France). 6 sera from *M. bovis* infected human tuberculous patients and 24 sera from BCG-vaccinated patients suffering from other pathologies were respectively obtained from Institut Pasteur, (Madagascar), and the Centre de Biologie Medicale spécialisée (CBMS) (Institut Pasteur, Paris). Sera from tuberculous cattle (*M. bovis* infected) were obtained from CNEVA, (Maison Alfort).

Subcloning Procedures

Restriction enzymes and T4 DNA ligase were purchased from Gibco/BRL, Boehringer Mannheim and New England Biolabs. All enzymes were used in accordance with the manufacturer's recommendations. A 1-kb ladder of DNA molecular mass markers was from Gibco/BRL. DNA fragments used in the cloning procedures were gel purified using the Geneclean II kit (BIO 101 Inc., La Jolla, Calif.). Cosmids and plasmids were isolated by alkaline lysis (Sambrook et al., 1989). Bacterial strains were transformed by electroporation using the Gene Pulser unit (Bio-Rad Laboratories, Richmond, Calif.).

BRIEF DESCRIPTION OF THE DRAWINGS

FIG. 2 shows the nucleotide (SEQ ID NO:1) and derived amino acid (SEQ ID NO:2) sequences of the *M. tuberculosis* des gene.

FIG. 3 shows a comparative sequence analysis of class II diiron-oxo proteins and the *M. tuberculosis* Des protein.

Shaded residues indicate cluster ligands and probable iron ligands in the *M. tuberculosis* Des protein. Bold unshaded framed letters are probable residues involved in the network of hydrogen bonds to the cluster. Other bold letters indicate conserved residues that are believed to participate in the O2-binding site. Gaps introduced into the sequence of Des are indicated by dots. Accession numbers are as follows: ribonucleotide reductases: v01555, Epstein-barr virus; k02672, *E. Coli*. Methane monooxygenase hydroxylases: M58499, *Methylococcus capsulatus*; X55394, mmoX *Methylosinus trichosporium*; M60276, Pseudomonas sp. strain CF 600 phenol hydroxylase dmpN polypeptide; M65106, *Pseudomonas mendocina* KR1. Stearoyl-ACP desaturases: M59857, *Ricinus communis*; M59858, cucumber; M61109, safflower; X62898, spinach; X60978, Brassica; M91238, potato; X70962, linseed; M93115, coriander Delta-4 desaturase.

Figure 1:
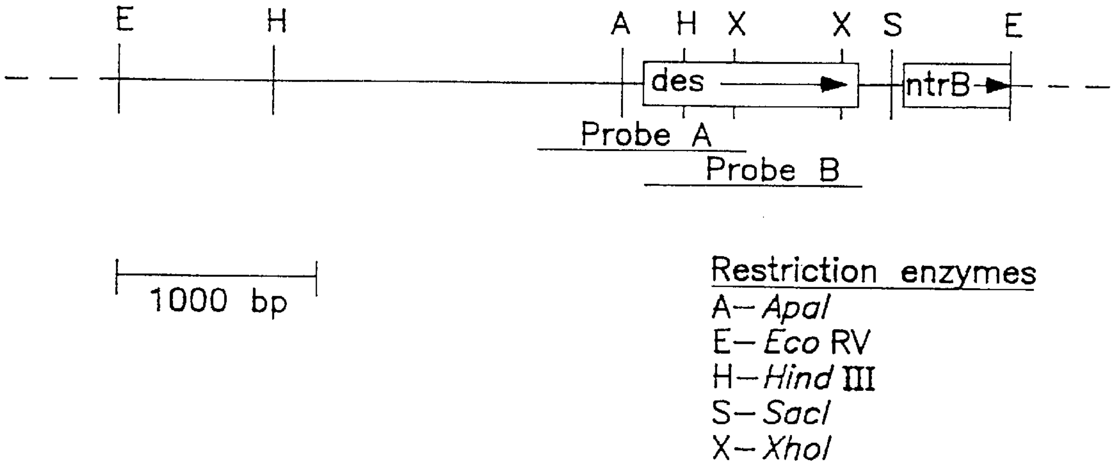
FIG. 1 is a restriction map of the 4.5 kb EcoRV fragment encoding the *M. tuberculosis* des gene.
Figure 4:
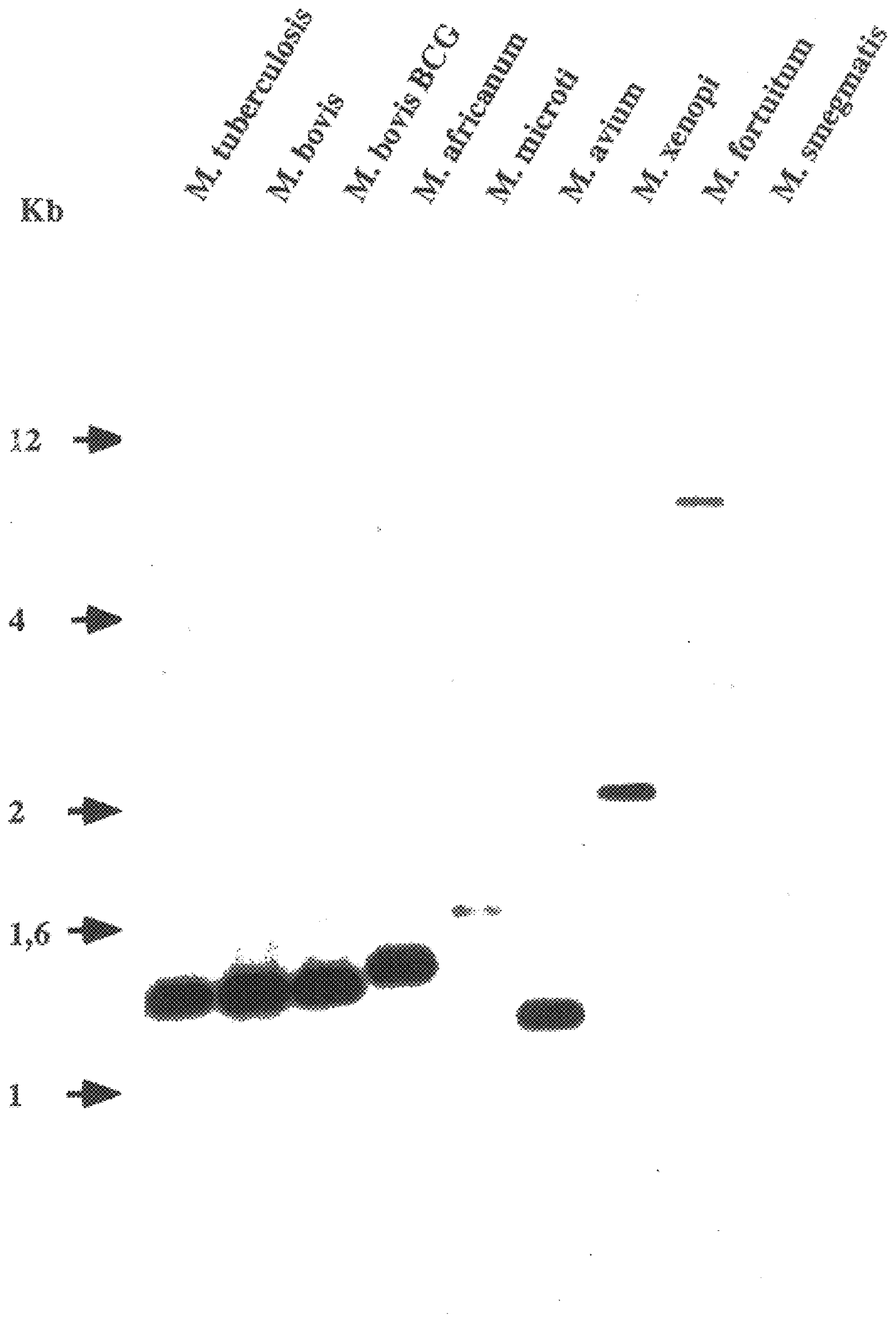

FIG. 4 is a Southern blot analysis of the distribution of the des gene in other mycobacterial species. DNA from various mycobacterial strains were Pstl-digested, electrophoresed, transferred onto a nylon membrane by Southern blotting, and hybridized using probe B, which is shown in FIG. 1.

Figure 5:
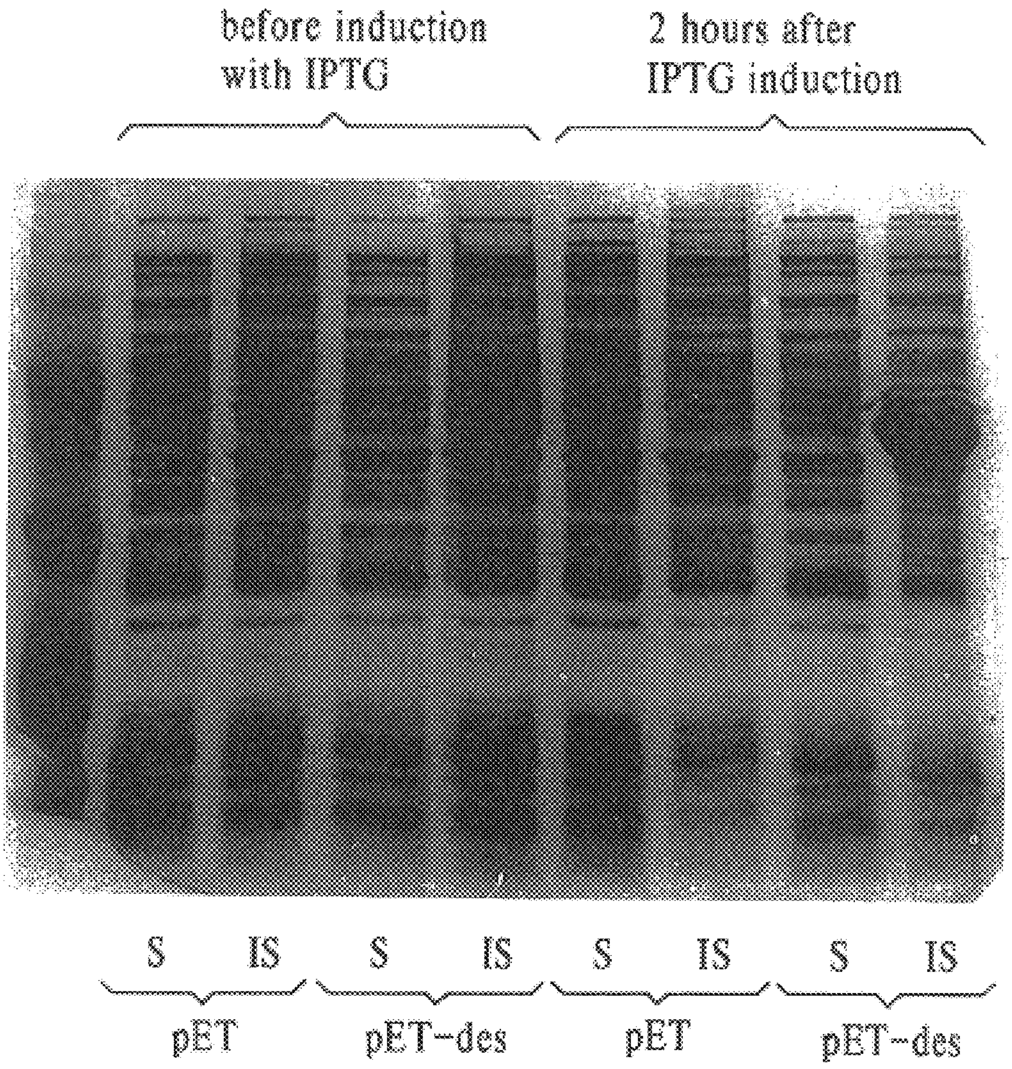

FIG. 5 shows an SDS-PAGE gel of soluble and insoluble extracts from *E. coli* expressing the DES protein on plasmid pETdes (I-1718).

Figure 6:
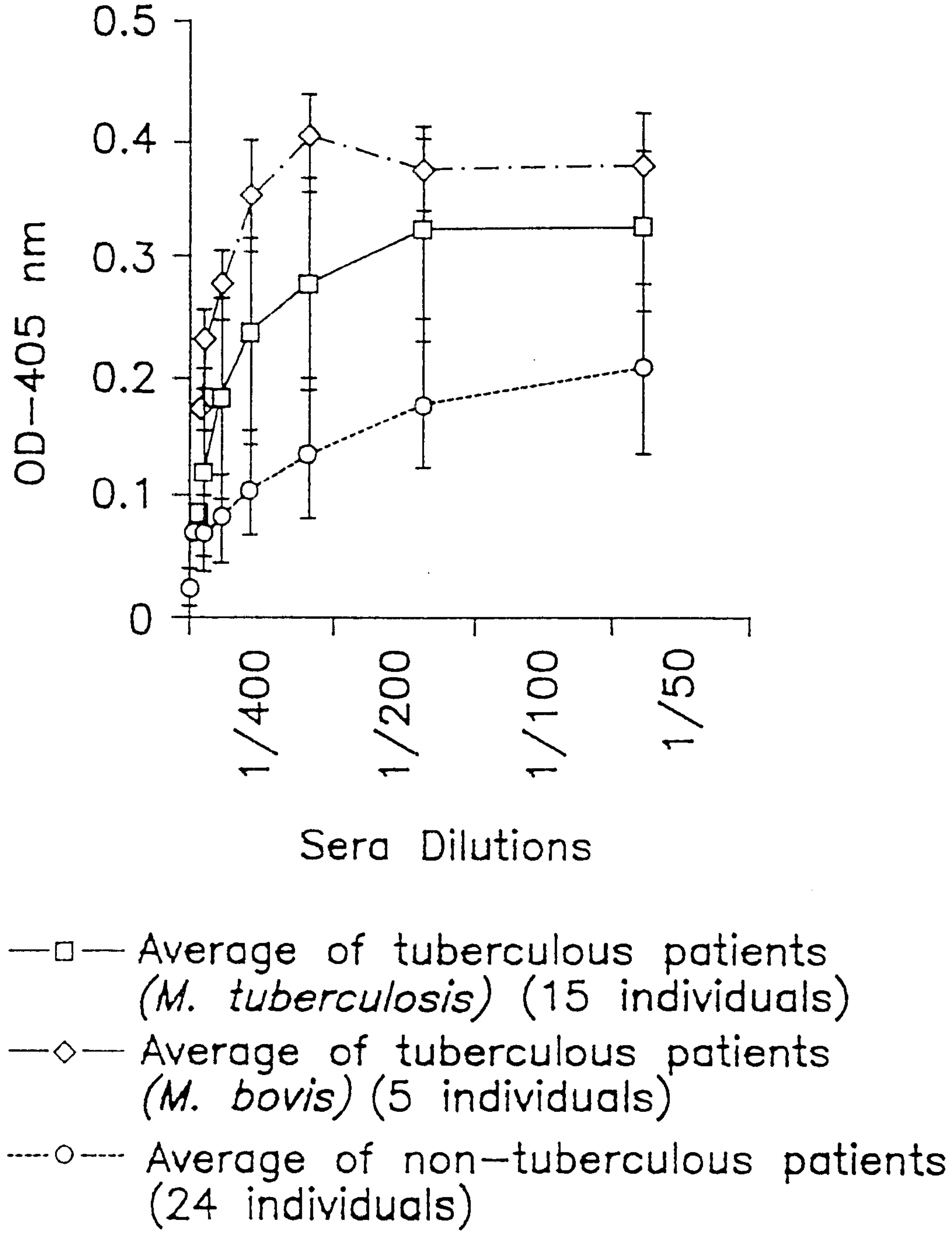

FIG. 6 shows the results of ELISAs of the sensitivity of the antibody response to the DES antigen of human tuberculous and non-tuberculous patients.

FIG. 7 shows the nucleotide and derived amino acid sequence of the *Mycoplasma tuberculosis* des gene. The underlined sequences correspond to the −35 and −10 boxes of the promoter and a Shine Dalgarno sequence that corresponds to the putative ribosomal attachment site, respectively. The adenosine labelled "+1" corresponds to the transcription initiation site.

FIG. 8 is a table of the bacterial strains and plasmids used in this application.

Figure 9:
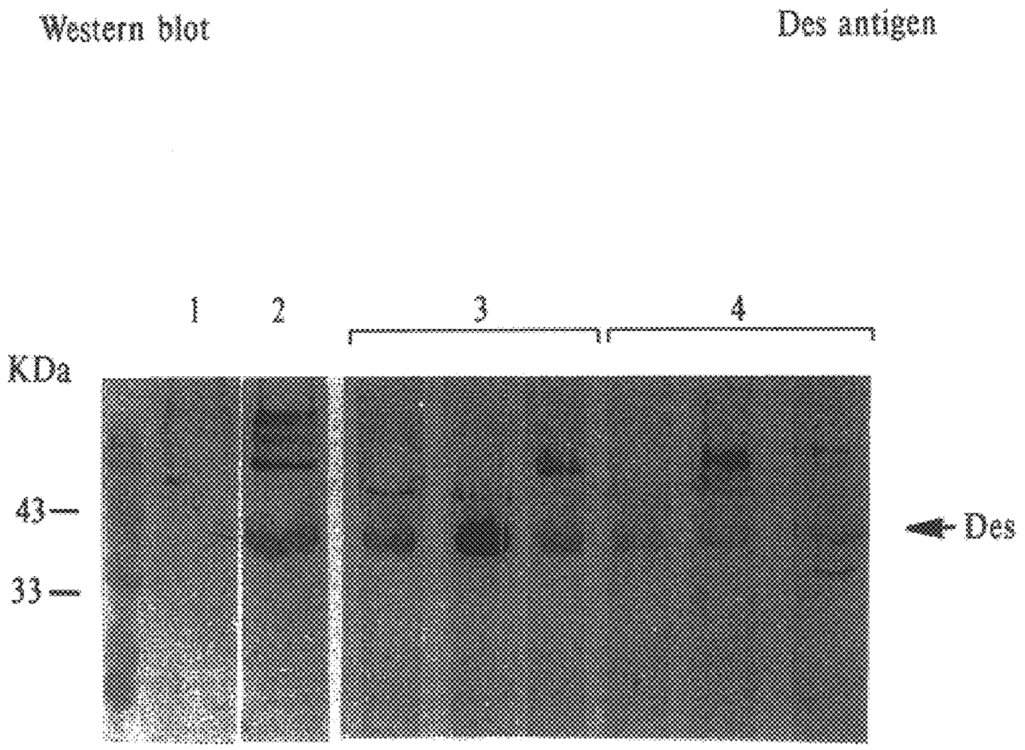

FIG. 9 is a Western blot showing the recognition of the purified DES protein by antibodies from *M. bovis* and *M. tuberculosis*-infected humans and cattle.

SOUTHERN BLOT ANALYSIS AND COLONY HYBRIDIZATION

DNA fragments for radiolabeling were separated on 0.7% agarose gels (Gibco BRL) in a Tris-borate-EDTA buffer system (Sambrook et al., 1989) and isolated from the gel by using Geneclean II (BIO 101). Radiolabeling was carried out with the random primed labeling kit Megaprime (Amersham) with 5 $\mu$Ci of ($\alpha$-$^{32}$P)dCTP, and nonincorporated label was removed by passing through a Nick Column (Pharmacia). Southern blotting was carried out in 0.4 M NaOH with nylon membranes (Hybond-N+, Amersham) according to the Southern technique (Southern, 1975), prehybridization and hybridization was carried out as recommended by the manufacturer using RHB buffer (Amersham). Washing at 65° C. was as follows: two washes with 2×SSPE (150 mM NaCl, 8.8 mM $NaH_2PO_4$, 1 mM EDTA pH 7.4)-SDS 0.1% of 15 minutes each, one wash with 1×SSPE-SDS 0.1% for 10 minutes, two washes with 0.7× SSPE-SDS 0.1% of 15 minutes each. Autoradiographs were prepared by exposure with X-ray film (Kodak X-Omat AR) at −80° C. overnight. Colony hybrization was carried out using nylon membrane discs (Hybond-N+0.45 $\mu$m, Amersham). *E. coli* colonies adsorbed on the membranes were lysed in a (0.5 M NaOH, 1.5 M NaCl) solution, before being placed for one minute in a micro-wave oven to fix the DNA. Hybridization and washings were as described for the Southern blotting analysis.

DNA Sequencing and Analysis

Sequences of double-stranded plasmid DNA were determined by the dideoxy-chain termination method (Sanger et al., 1977) using the Taq Dye Deoxy Terminator Cycle sequencing Kit (Applied Biosysterns), on a GeneAmp PCR System 9600 (Perkin Elmer), and run on a DNA Analysis System-Model 373 stretch (Applied Biosystems). The sequence was assembled and processed using DNA strider™ (CEA, France) and the University of Wisconsin Genetics Computer Group (UWGCG) packages. The BLAST algorithm (Altschul et al., 1990) was used to search protein data bases for similarity.

Expression and Purification of the DES Protein in *E. coli*

A 1043 bp NdeI-BamHI fragment of the des gene was amplified by PCR using nucleotides JD8 (5'-GGCATATICAGCCAAGCTGACOGACCTGCAG-3') (SEQ ID NO:3) and JD9 (5'-CCGGGATCCCGCGCTCGCCGCTCTGCATCGTCG-3'), and cloned into the NdeI-BamHI sites of pET14b (Novagen) to generate pET-des. PCR amplifications were carried out in a DNA thermal Cycler (Perkin Elmer), using Taq polymerase (Cetus) according to the manufacturer's recommendations. PCR consisted of one cycle of denaturation (95° C., 6 min) followed by 25 cycles of amplification consisting of denaturation (95° C., 1 min), annealing (57° C., 1 min), and primer extension (72° C., 1 min). In the pET-des vector, the expression of the des gene is under control of the T7 bacteriophage promoter and the DES antigen is expressed as a fusion protein containing six histidine residues. Expression of the des gene was induced by addition of 0.4 mM IPTG in the culture medium. The DES protein was purified by using a nickel-chelate affinity resin according to the recommendations of the supplier (Qiagen, Chatsworth, Calif.). Linked to the localization of the DES protein in cytoplasmic inclusion bodies, the purification was carried out under denaturating conditions in guanidine hydrochloride buffers. The protein was eluted in buffer A (6 M guanidine hydrochloride. 0.1 M $NaH_2PO_4$, 0.01 M Tris, pH 8) containing 100 mM EDTA. The purified protein was kept and used in buffer A, as all attempts to solubilize it in other buffers were unsuccessful.

SDS-PAGE and Immunoblotting

Sodium dodecyl sulfate-polyacrylamide gel electrophoresis (SDS-PAGE) was carried out as described by Laemmli (1970). For Western blotting experiments (immunoblotting), approximately 10 $\mu$g of DES purified protein were run on a SDS-polyacrylamide gel and transferred onto nitrocellulose membranes (Hybond C extra, Amersham) using a Bio-Rad mini transblot apparatus according to the recommendations of the manufacturer (Bio-Rad Laboratories, Richmond, Calif.). Transfer yield was visualized by transient staining with Ponceau Rouge. The membrane were incubated with human patient or cattle sera diluted 1/200$^e$ at 37° C. for 1 hour and with a goat anti-human (Promega) or rabbit anti-cattle (Biosys)IgG alkaline phosphatase-conjugated secondary antibody diluted 1/2500$^e$ for 30 minutes at 37° C. The color reaction was performed by addition of 5-bromo-4-chloro-3-indolylphosphate (0.165 mg/ml) and toluidinum nitroblue tetrazolium (0.33 mg/ml) as substrates.

ELISA

The human or cattle sera were tested for antibodies against DES by enzyme-linked immunosorbent assay (ELISA). The 96-well micro-titer trays (Nunc) were coated with 0.1 μg (per well) of purified DES protein in guanidine hydrochloride buffer A (6 M guanidine hydrochloride, 0.1 M $NaH_2PO_4$, 0.01 M Tris, pH 8) (1 h at 37° C. and 16 h at 4° C.). After three washes, wells were saturated with bovine serum albumin 3% in phosphate buffered saline (PBS) for 30 mn at room temperature. After three washes, sera diluted from $1/50^e$ to $1/3200^e$ in buffer (PBS, 0.1% Tween 20, 1% bovine serum albumin) were added to the wells for 2h at 37° C. After three washes, the wells were treated with goat anti-human IgG-alkaline phosphatase conjugate (Promega) diluted $1/4000^e$ for 1 h at 37° C. Then, 4 mg of p-nitrophenylphosphate per ml were added as substrate. After 20 mn of incubation at 37° C., the plates were read photometrically at an optical density of 405 nm in micro-ELISA Autoreader (Dynatech, Marnes la Coquette, France).

Statistics

Antibody response of the different sera tested were compared by using the Student t test. $P \geqq 0.05$ was considered nonsignificant.

Nucleotide Sequence and Accession Number

The nucleotide sequences of des has been deposited in the Genome Sequence Data Base (GSDB) under the accession number U49839.

Cloning of the Des Gene

The construction of a library of fusions of *M. tuberculosis* genomic DNA to the phoA gene and its expression in *M. smegmatis*, described by Lim et al. (1995), led to the isolation of several $PhoA^+$ clones. pExp421 is the plasmid harboured by one of the $PhoA^+$ clones selected from this library. Detection of enzymatically active alkaline phosphatase indicated that the pExp421 insert contains functional expression and exportation signals. Restriction analysis showed that pExp421 carries a 1.1 kb insert. Partial determination of its sequence identified a 577 bp ORF, named des, fused in frame to the phoA gene and presenting two motifs, of 9 and 14 amino acids, conserved with soluble stearoyl-acyl-carrier protein desaturases (Lim et al., 1995).

To isolate the full-lengh des gene, the *M. tuberculosis* H37Rv pYUB18 genomic cosmid library (Jacobs et al., 1991), was screened by colony hydridization with the 1.1 kb probe (probe A, see FIG. 1). Two hybridizing cosmids named $C_3$ and $C_4$ were selected for further isolation of the gene. $C_3$ and $C_4$ were cut with several restriction enzymes and subjected to Southern blot analysis using the 1.1 kb fragment as a probe.

The EcoRV restriction profile revealed a single hybridizing fragment of 4.5 kb which was subcloned into pBluescript $KS^+$ (Stratagene) to give plasmid pBS-des.

Characterization of the Des Gene

The DNA sequence of the full des ORF was determined (FIG. 2). The des gene was shown to cover a 1017 bp region, encoding a 339 amino acid protein with a calculated molecular mass of 37 kDa. The ORF starts with a potential ATG start codon at position 549, and ends with a TAG stop codon at position 1565. There is a potential Shine-Dalgamo motif (GGAGG) at position −8 upstream of the ATG. The G+C content of the ORF (62%) is consistent with the global GC content observed in mycobacterial genome. The nucleotide and deduced amino acid sequences of the des gene were compared to sequences in databases. They showed very high homologies to the *M. leprae* aadX gene located on cosmid B2266, deposited in GenBank as part of the *M. leprae* genome sequencing project (GenBank accession number n° U15182). Within the coding region, the DNA sequences were 79% identical while the encoded proteins were 80% identical (88% including conserved residues). The des gene also scored significantly against soluble stearoyl-ACP desaturases: 44% identity at the nucleotide level, 30% identity (51% including conserved residues) at the amino acid level, to the *Oryza sativa* stearoyl-ACP desaturase (accession n° D38753).

Although the detection of a phoA enzymatical activity in the *M. smegmatis* clone harbouring the pExp421 suggests the DES protein is exported, no structural similarities were found between the DES protein N terminal amino acids and signal sequences of bacterial exported proteins (Izard & Kendall, 1994).

Like in *M. leprae* genome, a second ORF presenting high homologies to the *M. leprae* putative NtrB gene (cosmnid B2266), is located downstream of the des gene in *M. tuberculosis* FIG. 2. Interestingly, the two ORF, des and "NtrB", are separated in *M. tuberculosis* by two direct repeats of 66 nucleotides overlapping on 9 nucleotides (FIG. 2). Although *M. leprae* and *M. tuberculosis* seem to share the same genomic organization in this part of the chromosome, these repeats are absent from the *M. leprae* genome.

The Des Protein Presents the Conserved Amino Acid Motifs of the Class II Diiron-oxo Proteins Further analysis of the amino-acid sequence of the DES protein revealed the presence of conserved motifs found only in class II diiron-oxo proteins (Fox et al., 1994) (FIG. 3). These proteins are oxo-bridged diuron clusters (Fe—O—Fe) containing proteins. They possess in their secondary structure 4 alpha helices involved in the protein-derived cluster ligands. As revealed by X-ray structure studies, in these proteins, the diiron axis is oriented parallel to the long axis of the four helix bundle with ligands arising from four noncontiguous helices, B, C, E and F. *M. tuberculosis* DES protein appears to have the same active site residues as the class II diiron-oxo enzymes. This includes Glu and His residues ($E_{107}$ and $H_{110}$ in helix C, $E_{167}$ in helix E and $E_{197}$ and $H_{200}$ in helix F) that are ligands to the iron atoms, Asp, Glu and Arg residues ($E_{106}$ and $R_{109}$ in helix C, $D_{196}$ in helix F) that are involved in a hydrogen-bonding network to the cluster and, lie and Thr residues that may be part of the $O_2$-binding site ($T_{170}$ in helix E, $I_{193}$ in helix F). Thus, the *M. tuberculosis* DES protein contains in its primary sequence two conserved D/E(ENXH) motifs separated by 85 amino acids.

The class II diiron-oxo protein family contains up to date ribonucleotide reductases, hydrocarbon hydroxylases (methane monooxygenase, toluene-4-monooxygenase and phenol hydroxylase) and soluble-ACP desaturases. On the overall sequence alignment the DES protein presents higher homology to soluble stearoyl-ACP desaturases than to ribonucleotide reductases or bacterial hydroxylases. The percentage identity at the amino acid level of the DES protein was said to be 30% with the *Oryza sativa* stearoyl-ACP desaturase, whereas it is only 17% with the *Methylococcus capsulatus* methane monooxygenase (accession n° M58499), 17.5% with the Pseudomonas sp CF 600 phenol hydroxylase (accession n° M60276) and 17.7% with the Epstein Barr ribonucleotide reductase (accession n° V01555). Homologies to the soluble Δ9 desaturases mostly concern the amino acids located within the active site in helices C, E and F (FIG. 3).

Distribution of the Des Gene in Other Mycobacterial Species

The presence of the des gene in PstI-digested chromosomal DNA from various mycobacterial strains was analyzed by Southern blotting (FIG. 4). The probe used (probe B) is a PCR amplification product corresponding to nucleotides 572 to 1589 (see FIG. 1). The probe hybridized on all mycobacterial genomic DNA tested. Strong signals were detected in *M. tuberculosis, M. bovis, M. bovis* BCG, *M. Africanum* and *M. avium*. Weaker signals were visible in *M. microti, M. xenopi, M. fortuitum* and *M. smegmatis*. Thus, the des gene seems to be present in single copy at least in the slow growing *M. tuberculosis, M. bovis, M. bovis* BCG, *M. Africanum. M. avium* and *M. xenopi* as well as in the fast growing *M. smegmatis.*

Expression of the Des Gene in *E. coli*

In order to overexpress the DES protein, the des gene was subcloned into the bacteriophage T7 promoter-based expression vector pET14b (Novagen). A PCR amplification product of the des gene (see material and methods) was cloned into the NdeI-BamHI sites of the vector, leading to plasmid pET-des. Upon IPTG induction of *E. coli* BL21 DE3 pLysS cells harbouring the plasmid pET-des, a protein of about 40 kDa was overproduced. The size of the overproduced protein is in agreement with the molecular mass calculated from the deduced polypeptide. As shown in FIG. 5, the great majority of the overproduced DES protein is present in the insoluble matter of *E. coli* cells. This probably results from the precipitation of the over-concentrated protein in *E. coli* cytoplasm thus forming inclusion bodies. To be able to dissolve the protein, the purification was carried out using a nickel chelate affinity resin under denaturating conditions in guanidine hydrochloride buffers. Among all the conditions tested (pH, detergents . . . ), the only condition in which the protein could be eluted without precipitating in the column and remain soluble, was in a buffer containing 6 M guanidine hydrochloride.

Immunogenicity of the DES Protein after Infection 20 serum samples from *M. tuberculosis* infected human patients (4 with extra-pulmonary tuberculosis, 15 with pulmonary tuberculosis and 1 with both forms if the disease), 6 sera from *M. bovis* infected human patients and 4 sera from *M. bovis* infected cattle were tested either pooled or taken individually in immunoblot experiments to determine the frequency of recognition of the purified DES protein by antibodies from infected humans or cattle. 20 out of the 20 sera from the *M. tuberculosis* infected human patients and 6 out of the 6 sera from the *M. bovis* infected human patients recognized the recombinant antigen as shown by the reaction with the 37 kDa band (FIG. 9). Furthermore, a pool of sera from human lepromatous leprosy patients also reacted against the DES antigen.

In contrast, the pool of serum specimens from *M. bovis* infected cattle did not recognize the DES protein. These results indicate that the DES protein is highly immunogenic in tuberculosis human patients. Both pulmonary and extra-pulmonary tuberculosis patients recognize the antigen.

Magnitude of Human Patients Antibody Response

An enzyme-linked immunosorbent assay (ELISA) was used to compare the sensitivity of the different serum samples from 20 tuberculosis patients (15 infected by *M. tuberculosis* and 5 infected by *M. bovis*) to the DES antigen. This technique was also carried out to compare the sensitivity of the antibody response to DES of the 20 tuberculosis patients to the one of 24 patients (BCG-vaccinated) suffering from other pathologies. As shown on FIG. 6, patients suffering from other pathologies than tuberculosis, react at a low level to the DES antigen (average $OD_{405}$=0.17 for a scrum dilution 1/100$^e$). The average antibody response from the tuberculosis patients infected by *M. tuberculosis* or *M. bovis* against the same antigen is much more sensitive ($OD_{405}$=0.32 and $OD_{405}$=0.36 respectively, for a serum dilution 1/100$^e$). This difference in the sensitivity of the immunological response is statistically highly significant at every dilution from 1/50$^e$ to 1/3200$^e$ as shown by a Student $t_{95}$ test ($t_{95}$=5.18, 6.57, 6.16, 5.79, 4.43, 2.53 and 1.95, at sera dilutions 1/50$^e$, 1/100$^e$, 1/200$^e$, 1/400$^e$, 1/800$^e$. 1/1600$^e$ and 1/3200$^e$, respectively).

No differences in the sensitivity of the antibody response was noticed between patients suffering from pulmonary or extra-pulmonary tuberculosis.

The PhoA gene fusion methodology permitted the identification of a new *M. tuberculosis* exported antigenic protein.

This 37 kDa protein contains conserved amino acid residues which are characteristical of class II diiron-oxo-proteins. Proteins from that family are all enzymes that require iron for activity. They include ribonucleotide reductases, hydrocarbon hydroxylases and stearoyl-ACP desaturases. The *M. tuberculosis* DES protein only presents significant homologies to plant stearoyl-ACP desaturases (44% identity at the nucleotide level, and 30% identity at the amino-acid level) which are also exported enzymes as they are translocated across the chloroplastic membranes (Keegstra & Olsen, 1989). This result suggests that the DES protein could be involved in the mycobacterial fatty acid biosynthesis. Furthermore, the localization of the protein outside the cytoplasm would be consistent with its role in the lipid metabolism, since lipids represent 60% of the cell wall constituents and that part of the biosynthesis of the voluminous mycolic acids containing 60 to 90 carbon atoms occurs outside the cytoplasm. Among all the different steps of the lipid metabolism, desaturation reactions are of special interest, first because they very often take place at early steps of lipid biosynthesis and secondly because, through the control they have on the unsaturation rate of membranes, they contribute to the adaptation of mycobacteria to their environment (Wheeler & Ratledge, 1994). An enzyme system involving a stearoyl-Coenzyme A desaturase (analog of the plant stearoyl-ACP-desaturases), catalyzing oxydative desaturation of the CoA derivatives of stearic and palmitic acid to the corresponding Δ9 monounsatured fatty acids has been biochemically characterized in *Mycobacterium phlei* (Fulco & Bloch, 1962 ; Fulco & Bloch, 1964 ; Kashiwabara & al., 1975 Kashiwabara & Sato, 1973). This system was shown to be firmly bound to a membranous structure (Fulco & Bloch, 1964). Thus, *M. tuberculosis* stearoyl-Coenzymne A desaturase (Δ9 desaturase) is expected to be an exported protein. Sonicated extracts of *E. coli* expressing the DES protein were assayed for Δ9 desaturating activity according to the method described by Legrand and Besadoun (1991), using (stearoyl-CoA) $^{14}C$ as a substrate. However, no Δ9 desaturating activity could be detected. This result is probably linked to the fact desaturation systems are multi-enzyme complexes involving electron transport chains and numerous cofactors, often difficult to render functional in vitro. *E. coli* and mycobacteria being very different from a lipid metabolism point of view, the *M. tuberculosis* recombinant Δ9 desaturase might not dispose in *E. coli* of all the cofactors and associated enzymes required for activity or might not interact properly with them. Moreover, not all cofactors involved in the Δ9 desaturation process of mycobacteria are known, and they might be missing in the incubation medium.

However, if the DES protein encodes a Δ9 desaturase. an amazing point concerns its primary sequence. Indeed, all animal, fungal and the only two bacterial Δ9 desaturases sequenced to date (Sakamoto et al., 1994) are integral membrane proteins which have been classified into a third class of diiron-oxo proteins on the basis of their primary sequences involving histidine conserved residues (Shanklin et al., 1994). The plant soluble Δ9 desaturases are the only desaturases to possess the type of primary sequence of class II diiron-oxo proteins (Shanklin & Somerville. 1991). No bacteria have vet been found which have a plant type Δ9 desaturase.

As shown by immunoblotting and ELISA experiments, the DES protein is a highly immunogenic antigen which elicits B cell response in 100% of the tuberculosis *M. bovis* or *M. tuberculosis*-infected human patients tested, independently of the form of the disease (extrapulmonary or pulmonary). It also elicits an antibody response in lepromatous leprosy patients. Interestingly, although more sera would need to be tested, tuberculous cattle do not seem to recognize the DES antigen. Furthermore, the ELISA experiments showed that it is possible to distinguish tuberculosis patients from patients suffering from other pathologies on the basis of the sensitivity of their antibody response to the DES antigen. The DES antigen is therefore a good candidate to be used for serodiagnosis of tuberculosis in human patients. The reason why the non-tuberculous patients tested recognize at a low level the DES protein could be due to the fact they are all BCG-vaccinated individuals (BCG expressing the protein), or to a cross-reactivity of their antibody response with other bacterial antigens. It would now be interesting to know whether the DES antigen possesses in addition to its B cell epitotes. T cell epitotes which are the only protective ones in the host immunological response against pathogenic mycobacteria. If the DES protein is also a good stimulator of the T cell response in a majority of tuberculosis patients, it could be used either individually or as part of a "cocktail" of antigens in the design of a subunit vaccine against tuberculosis.

The references cited herein are listed on the following pages and are expressly incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

1 Altschul. S. F., W. Gish, W. Millers E. M. Myers, and D. J. Lipman, 1990. Basic local alignment search tool. Journal of Molecular Biology. 215:403–410.

2. Andersen, A. B., and P. Brennan, 1994. Proteins and antigens of *Mycobactenum tuberculosis*, p. 307–332. In B. R. Bloom (ed.), Tuberculosis :Pathogenesis, Protection, and Control. ASM, Washington, DC.

3. Andersen, P. 1994. Effective vaccination of mice against *Mycobactenum tuberculosis* infection with a soluble mixture of secreted mycobacterial proteins. Infect. Immun. 62:2536–2544.

4. Berthet, F. X., J. Rauzier, E. M. Lim, W. Philipp, B. Gicquel, and D. Portaoï, 1995. Charactenzation of the *M. tuberculosis* erp gene encoding a potential cell surface protein with repetitive structures. Microbiology, 141:2123–2130.

5. Braibant, M., L. D. Wit, P. Peirs, M. Kalai, J. Ooms, A. Drowart, K. Huygen, and J. Content, 1994. Structure of the *Mycobacterium tuberculosis* antigen 88, a protein related to the *Escherichia coli* PstA periplasmic phosphate permease subunit, Infection and Immunity, 62:849–854.

6. Fox, B. G., J. Shanklin, J. Ali, T. M. Loerh, and J. Sanders-Loerb, 1994. Resonance Raman evidence for an Fe—O—Fe center in stearoyl-ACP desaturase. Primary sequence identity with other diiron-oxo proteins. Biochemistry 33:12776–12786.

7. Fulco, A. J., and K. Bloch, 1962. Cofactor requirements for fatty acid desaturation in *Mycobacreriumphlei*. Biochim. Biophys. Acta. 63:545–546.

8. Fulco, A. J., and K. Bloch, 1964. Coactor requirements for the formation of Δ9 unsatured fatty acids in *Mycobactenum phiei*. The Journal of Biological Chemistry. 239:993–997.

9. Haslov, K., A. Andersen, S. Nagai, A. Gottschau, T. Sorensen, and P. Andersen, 1995. Guinea pig cellular immune responses to proteins secreted by *Mycobactenum tuberculosis*. Infection and Immunity, 63:804–810.

10. Hatfull, G. F. 1993. Genetic transformation of mycobacteria. Trends in microbiology, 1:310–314.

11. Hermans, P. W. M., F. Abebe, V. I. O. Kuteyi, A. H. J. Kolk, J. E. R. Thole, and M. Harboe, 1995. Molecular and immunological characterization of the highly conserved antigen 84 from *Mycobacterium tuberculosis* and *Mycobacterium leprae*. Infection and Immunity, 63:954–960.

12. Izaril J. W., and D. A. Kendall, 1994. Signal peptides: exquisitely designed transport promoters. Molecular Microbiology, 13:765–773.

13. Jacobs, W. R., G. V. Kalpana. J. D. Cirillo. L. Pascopella, S. B. Snapper, R. A. Udam, W. Jones, R. G. Barletta, and B. R. Bloom, 1991. Genetic systems for mycobacteria. Methods enzymol. 204:537–555.

14. Kashiwabara, Y., H. Nakagawa, G. Matsuki, and R. Sato, 1975. Effect of metal ions in the culture medium on the stearoyl-Coenzyme A desaturase activity of *Mycobactenum phlei*. J. Biochem. 78:803–810.

15. Kashiwabara, Y., and R. Sato, 1973. Electron transfer mechanism involved in stearoyl-coenzyme A desaturation by particulate fraction of *Mycobactenum phiei*. J. Biochem. 74:405–413.

16 Keegstra, K., and L. J. Olsen, 1989. Chloroplastic precursors and their transport across the envelope membranes. Ann. Rev. Plant Physiol. Plant Mol. Biol. 40:471–501.

17. Laemmli. U. K. 1970. Cleavage of structural proteins during the assembly of the head of bacteriophage T4. Nature (London). 227:680–685.

18. Lee. B. Y., S. A. Hefta, and P. J. Brennan, 1992. Characterization of the major membrane protein of virulent *Mycobacterium tuberculosis*. Infection and Immunity. 60:2066–2074.

19. Legrand, P., and A. Bensadoun, 1991. Stearyl-CoA desaturase activity in cultured rat hepatoytes. Biochimica et Biophysica Acta. 1086:89–94.

20. Lim, E. M., J. Rauzier, J. Timm, G. Torrea. A. Murray, B. Gicquel, and D. Portnmï, 1995. Identification of *Mycobactenum tuberculosis* DNA sequences encoding exported proteins by using phoA gene fusions. Journal of Bacteriology. 177:59–65.

21. Pal, P. G., and M. A. Horwitz, 1992. Immunization with extracellular proteins of *Mycobacterium tuberculosis* induces cell-mediate immune responses and substential protective immunity in a guinea pig model of puny tuberculosis. Infection and Immunity. 60:4781–4792.

22. Roman, F., A. Laqueyrerie, P. Militzer, P. Pescher, P. Chavarot, M. Lagranderie, G. Auregan, M. Gheorghiu, and G. Marchal, 1993. Identification of a *Mycobactenum bovis* BCG 45/47-kilodalton antigen complex, an immunodommant target for antibody response after immunization with living bacteria. Infection and immunity 61:742–750.
23. Sakamoto, T., H. Wada, I. Nishida, M. Ohmori, and N. Murata, 1994. Δ9 acyl lipid desaturases of cyanobacteria. J. Biol. Chem. 269:25576–25580.
24. Sambrook, J., E. F. Fritsch, and T. Maniatis, 1989. Molecular cloning- A laboratory manual. Cold Spring Harbor Laboratory Press. Cold Spring Harbor, N.Y.
25. Sanger, F., S. Nicklen, and A. R. Coulson. 1977. DNA sequencing with chain terminating inhibitors. Proc. Natl. Acad. Sci. USA, 74:5463–5467.
26. Shanklin J., and C. Somerville, 1991. Stearoyl-acyl-carrier-protein desaturase from higher plants is structurally unrelated to the animal and fungal homologs. Proceeding of the National Academy of Science of the United States of America. 88:2510–2514.
27. Shanklin, J., E. Whittie, and B. G. Fox, 1994. Eight histidine residues are catalytically essential in a membrane-associated iron enzyme, stearoyl-CoA desaturase, and are conserved in alkane hydroxylase and xylene monooxygenase. Biochemistry. 33:12787–12794.
28. Snapper, S. B., B. R. Bloom. and J. W. R. Jacobs, 1990. Molecular genetic approaches to mycobacterial investigation, p. 199–218. In J. McFadden (ed.), Molecular Biology of the Mycobacteria. Surrey University Press, London.
29. Sorensen, A. L., S. Nagai, G. Houen, P. Andersen, and A. B. Andersen, 1995. Purification and characterization of a low-molecular-mass T-cell antigen secreted by *Mycobactenum tuberculosis*. Infection and Immunity 63:1710–1717.
30. Southern. E. M. 1975. Detection of specific sequences among DNA fragments separated by gel electrophoresis. J. Mol. Biol. 98:503–517.
31. Studier, W., A. H. Rosenberg, J. J. Dunn, and J. W. Dubendorff 1990. Use of T7 RNA polymerase to direct expression of cloned genes. Methods in Enzymology 185:60–89.
32. Thole, J. E. R., and R. v. d. Zee 1990, The 65 kD antigen: molecular studies on a ubiquitous antigen., p. 37–66. In J. McFadden (ed.). Molecular Biology of the mycobacteria. Surrey University Press, London.
33. Wheeler, P. R., and C. Ratledge. 1994. Metabolism of *Mycobacterium tuberculosis*, p. 353–385. In B. R. Bloom (ed.). Tuberculosis: Pathogenesis, Protection, and Control, ASM. Washington, D.C.
34. Young, D., T. Garbe, R. Lathigra and C. Abou-Zeid. 1990. Protein antigens: structure. function and regulation, p. 1–35. In J. McFadden (ed.), Molecular biology of mycobacteria. Surrey university Press, London.
35. Young, R. A., B. R. Bloom, C. M. Grossinsky, J. Ivany, D. Thomas, and R. W. Davis, 1985. Dissection of the *Mycobacterium tuberculosis* antigens using recombinant DNA. Proc. Natl. Acad. Sci. USA 82:2583–2587.

---

Proposed claims:

1. A process for the detection of antibodies present in a biological sample in a patient infected by bacteria of the *Mycobacterium genus* comprising a) bringing into contact a polypeptide or a peptide having the sequence of SEQ ID NO 2, which peptide is recognized by antibodies present in the sera of patients infected by bacteria of the *Mycobacterium genus*, with the biological sample; and b) detecting complexes formed between the polypeptide or peptide and the antibodies present in the biological sample.

2. The process according to claim 1, wherein the polypeptide or the peptide is recognized by antibodies present in the sera of patients infected by *Mycobacterium tuberculosis*.

3. The process according to claim 1, wherein the polypeptide or the peptide is recognized by antibodies present in the sera of patients infected by *Mycobacterium bovis*.

4. The process according to claim 1, wherein the polypeptide or the peptide is recognized by antibodies present in the sera of patients infected by *Mycobacterium leprae*.

* * * * *